United States Patent
Kraft et al.

(10) Patent No.: US 9,832,301 B2
(45) Date of Patent: Nov. 28, 2017

(54) SYSTEMS AND METHODS FOR ADJUSTING POWER LEVELS ON A MONITORING DEVICE

(71) Applicants: Haim Kraft, Hedera (IL); Leonid Usov, Natanya (IL)

(72) Inventors: Haim Kraft, Hedera (IL); Leonid Usov, Natanya (IL)

(73) Assignee: LABSTYLE INNOVATION LTD., Caesarea (IL)

( * ) Notice: Subject to any disclaimer, the term of this patent is extended or adjusted under 35 U.S.C. 154(b) by 0 days.

(21) Appl. No.: 15/050,581

(22) Filed: Feb. 23, 2016

(65) Prior Publication Data
US 2016/0248896 A1 Aug. 25, 2016

Related U.S. Application Data

(60) Provisional application No. 62/120,058, filed on Feb. 24, 2015.

(51) Int. Cl.
*H04W 52/02* (2009.01)
*H04M 1/725* (2006.01)
(Continued)

(52) U.S. Cl.
CPC ..... *H04M 1/72527* (2013.01); *A61B 5/14532* (2013.01); *A61B 10/0045* (2013.01);
(Continued)

(58) Field of Classification Search
CPC ........... H04M 1/72527; A61B 10/0045; A61B 5/14532; A61B 2560/0214; H04W 52/0225; Y02B 60/50
See application file for complete search history.

(56) References Cited

U.S. PATENT DOCUMENTS

| 2002/0013613 A1* | 1/2002 | Haller ................. A61B 5/0031 607/60 |
| 2008/0070599 A1 | 3/2008 | Apodaca et al. |

(Continued)

OTHER PUBLICATIONS

International Search Report for PCT Application No. PCT/IB2016/000236, dated Aug. 5, 2016.

*Primary Examiner* — Chuong A Ngo
(74) *Attorney, Agent, or Firm* — Greenberg Traurig LLP

(57) ABSTRACT

A system and method is provided for health management, for performing a parameter measurement in a fluid sample, including a mobile communications device with an application adapted to perform health management for one or more health related conditions; a strip adapted to absorb a fluid sample and to produce a signal indicative of the parameter level in the sample; and a fluid testing apparatus for obtaining an analog measurement of the fluid parameter, the fluid testing apparatus including an adaptor adapted to connect the strip to the mobile communications device to thereby allow delivery of the produced signal or a correlated signal to the mobile communications device for obtaining a measurement of the fluid parameter displayed on the mobile communications device, wherein the fluid testing apparatus relies on the mobile communications device for at least one of power supply and display means, and wherein the system includes a power level adjustment means associated with the device audio jack and/or the adaptor, for providing a suitable power output to operate the fluid testing apparatus.

11 Claims, 6 Drawing Sheets

(51) Int. Cl.
*A61B 10/00* (2006.01)
*A61B 5/145* (2006.01)

(52) U.S. Cl.
CPC . *H04W 52/0225* (2013.01); *A61B 2560/0214* (2013.01); *Y02B 60/50* (2013.01)

(56) References Cited

U.S. PATENT DOCUMENTS

| | | | |
|---|---|---|---|
| 2008/0139907 A1 | 6/2008 | Rao et al. | |
| 2010/0279418 A1 | 11/2010 | Larson et al. | |
| 2011/0054282 A1* | 3/2011 | Nekoomaram | A61B 5/0002 600/347 |
| 2012/0100887 A1* | 4/2012 | Tekin | A61B 5/0022 455/556.1 |

* cited by examiner

SYSTEMS AND METHODS FOR ADJUSTING POWER LEVELS ON A MONITORING DEVICE

CROSS REFERENCE TO RELATED APPLICATIONS

This application claims priority from U.S. Provisional Patent Application No. 62/120,058, filed Feb. 24, 2015, entitled "SYSTEMS AND METHODS FOR ADJUSTING POWER LEVELS ON A MONITORING DEVICE", which is incorporated in its entirety herein by reference.

FIELD OF THE INVENTION

The present invention relates to methods and devices useful in fluid testing.

BACKGROUND OF THE INVENTION

A medical device is an instrument, apparatus, implant, in vitro reagent, or similar or related article that is used to diagnose, prevent, or treat disease or other conditions, and does not achieve its purposes through chemical action within or on the body. With the rise of smartphone usage in the medical space, in 2013, the FDA issued to regulate mobile medical applications and protect users from their unintended use, soon followed by European and other regulatory agencies. This guidance distinguishes the apps subjected to regulation based on the marketing claims of the apps. Incorporation of the guidelines during the development phase of such apps can be considered as developing a medical device; the regulations have to adapt and propositions for expedite approval may be required due to the nature of 'versions' of mobile application development.

The terms medical software and medical device software may be considered undefined terms that can designate any software, software item or system used within a medical context (e.g. medical devices that monitor or control patients are predominantly controlled by software), depending on its intended use/indication for use. The terms "medical device software" or "software medical device" or, less commonly, "software-as-a-medical-device", may refer to a program or application or a product that is a standalone software system (not appended/integrated into a distinct product) AND meets the legal definition of a medical device (e.g. European medical devices directive MDD/93/42, updated in 2007 to explicitly include the term 'software').

The scope of the evolved regulatory definition of a medical device now explicitly includes the term "software" (and not simply software that is part of or within another product). As such, the following would be considered to fall under its scope: Software intended to analyze patient data generated by a medical device with a view to diagnosis and monitoring; Software that incorporates dosage algorithms for chronic conditions (e.g. diabetes); and Software intended for use by patients to diagnose or treat a physical or medical ailment (condition or disease).

It would be advantageous to use a smart phone as a medical device, making use of the audio jack on the smart phone or other computing device as a port for entering a medical instrument or sensor, thereby benefiting from the advantages to be gained by using the audio or earphone jack.

SUMMARY OF THE INVENTION

A system and method is provided for health management, for performing a parameter measurement in a fluid sample, including a mobile communications device with an application adapted to perform health management for one or more health related conditions; a strip adapted to absorb a fluid sample and to produce a signal indicative of the parameter level in the sample; and a fluid testing apparatus for obtaining an analog measurement of the fluid parameter, the fluid testing apparatus including an adaptor adapted to connect the strip to the mobile communications device to thereby allow delivery of the produced signal or a correlated signal to the mobile communications device for obtaining a measurement of the fluid parameter displayed on the mobile communications device, wherein the fluid testing apparatus relies on the mobile communications device for at least one of power supply and display means, and wherein the system includes a power level adjustment means associated with the device audio jack and/or the adaptor, for providing a suitable power output to operate the fluid testing apparatus.

In some embodiments, the power level adjustment means are adapted to modify the electrical power output from the communications device in measured/calculated increments.

In some embodiments, the power level adjustment means are adapted to modify the electrical power output from the communications device during a charging event of a fluid testing apparatus.

In some embodiments, the power level adjustment means are adapted to modify the electrical power output from the communications device substantially in real time.

In some embodiments, the power level adjustment means are adapted to dynamically modify the electrical power output from the communications device.

In some embodiments, the power level adjustment means are adapted to reduce printed circuit board heating of an audio-powered fluid resting apparatus, resulting from excessive electrical power input.

In some embodiments, the power level adjustment means are adapted to increased battery life of the mobile communications device.

In some embodiments, the power level adjustment means are adapted to reduce an output volume of electrical power provided by the mobile communications device.

In some embodiments, the power level adjustment means include a file with instructions to execute commands to enable execution of instructions to maximize efficiency of an output of electrical power for powering the FTA connected to the mobile device.

In some embodiments, the power level adjustment means is connected to a memory having stored therein power level adjustment data.

In further embodiments, a blood testing apparatus is provided, for performing glucose measurement in a blood sample comprising: a glucose strip adapted to absorb a blood sample and to produce a signal indicative of the glucose level in the blood sample; and an adaptor adapted to connect the glucose strip to a mobile communications device to thereby allow delivery of the produced signal or a correlated signal to the mobile communications device for obtaining a measurement of the glucose level displayed on the mobile communications device, wherein the blood testing apparatus relies on the mobile communications device at least for a power supply and display means, and wherein the mobile communications device includes a power level adjustment means associated with the device audio jack, for providing a suitable power output to operate the blood testing apparatus.

In still further embodiments, a method is provided for performing a fluid parameter measurement in a fluid sample comprising the steps of: installing a dedicated application software on a mobile communications device; loading a fluid sample on a fluid testing apparatus, the apparatus comprising: a strip adapted to absorb such sample and to produce a signal indicative of the parameter level in the sample; and an adaptor adapted to connect the strip to a smart phone to thereby allow delivery of the produced signal or a correlated signal to the mobile communications device for obtaining a measurement of the fluid parameter displayed on the mobile communications device, wherein the testing apparatus relies on the mobile communications device at least for a power supply and display means; inserting said loaded fluid testing apparatus into a headset jack of a mobile communications device to thereby allow communication between the apparatus and the mobile communications device and delivery of power supply; and obtaining the measured parameter level displayed on the smart mobile communications device; wherein the mobile communications device includes a power level adjustment means associated with the communications device audio jack, for providing a suitable power output to operate the fluid testing apparatus.

In some embodiments, the volume of the mobile communications device is automatically reduced to a selected level following an end of a fluid measurement process.

In further embodiments, a mobile hand held laboratory system is provided, capable of performing fluid parameter measurement of a sample, said system comprising: a mobile communications device installed with a dedicated application software; a strip adapted to absorb a fluid sample and to produce a signal indicative of said parameter level in the sample; and an adaptor adapted to connect the strip to a mobile communications device to thereby allow delivery of the produced signal or a correlated signal to the mobile communications device for obtaining a measurement of said fluid parameter displayed on the mobile communications device, wherein the testing apparatus relies on the mobile communications device for at least for a power supply and display means, and wherein the mobile communications device includes a power level adjustment means associated with the device audio jack, for providing a suitable power output to operate the fluid testing apparatus.

BRIEF DESCRIPTION OF THE DRAWINGS

The principles and operation of the system, apparatus, and method according to the present invention may be better understood with reference to the drawings, and the following description, it being understood that these drawings are given for illustrative purposes only and are not meant to be limiting, wherein.

Figure 1:
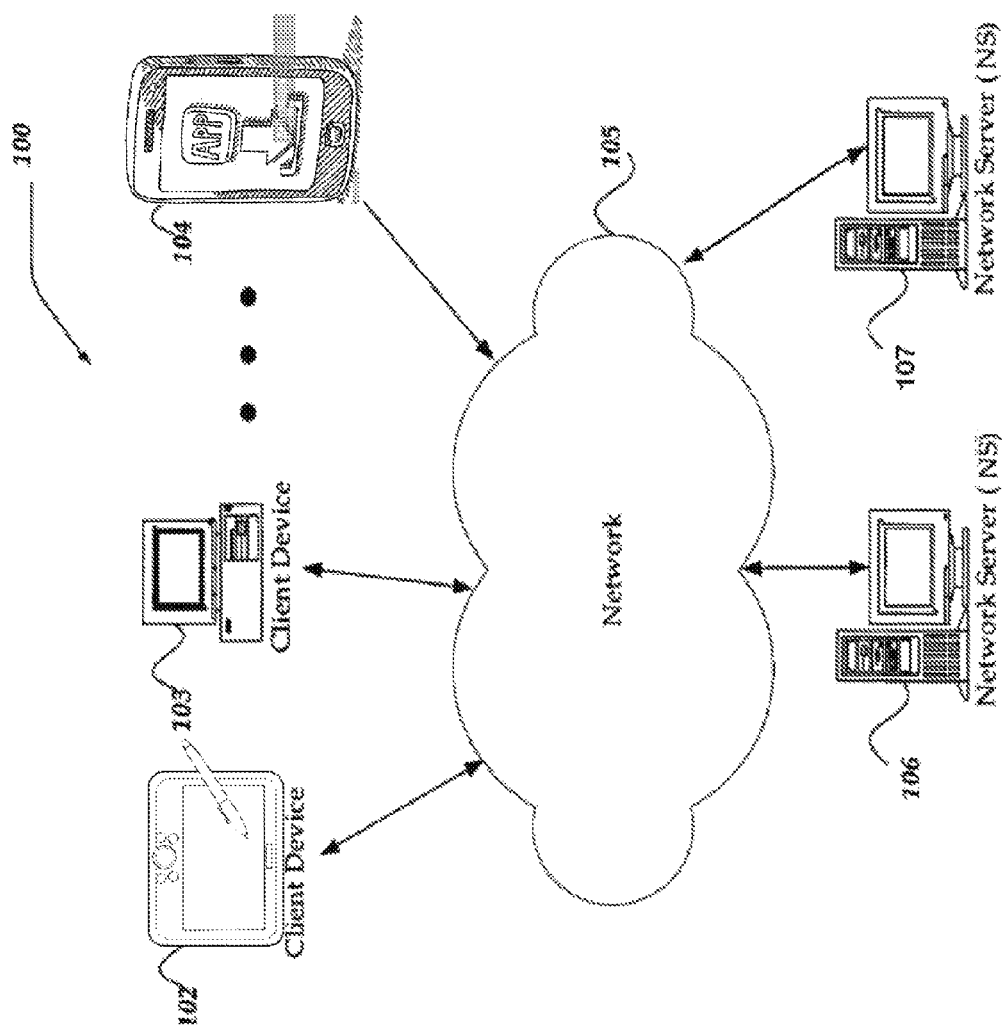
FIG. 1 is a schematic diagram of an example of a network environment in which the present invention may operate, according to some embodiments.

It will be appreciated that for simplicity and clarity of illustration, elements shown in the drawings have not necessarily been drawn to scale. For example, the dimensions of some of the elements may be exaggerated relative to other elements for clarity. Further, where considered appropriate, reference numerals may be repeated among the drawings to indicate corresponding or analogous elements throughout the serial views.

DESCRIPTION

The present invention will be further explained with reference to the attached drawings, wherein like structures are referred to by like numerals throughout the several views. The drawings shown are not necessarily to scale, with emphasis instead generally being placed upon illustrating the principles of the present invention. Further, some features may be exaggerated to show details of particular components.

The figures constitute a part of this specification and include illustrative embodiments of the present invention and illustrate various objects and features thereof. Further, the figures are not necessarily to scale, some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention which are intended to be illustrative, and not restrictive.

Throughout the specification and claims, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

It is understood that at least one aspect/functionality of various embodiments described herein can be performed in real-time and/or dynamically. As used herein, the term "real-time" is directed to an event/action that can occur instantaneously or almost instantaneously in time when another event/action has occurred. In some embodiments, the terms "instantaneous," "instantaneously," "instantly," and "in real time" refer to a condition where a time difference between a first time when an electrical power reading is transmitted and a second time when an adjustment to the electrical power reading is received is no more than 1 second. In some embodiments, the time difference between the electrical power reading and the adjustment is between less than 1 second and several seconds.

As used herein, the term "dynamic(ly)" means that events and/or actions can be triggered and/or occur without any human intervention. In some embodiments, events and/or actions in accordance with the present invention can be in real-time and/or based on a predetermined periodicity of at least one of: nanosecond, several nanoseconds, millisecond, several milliseconds, second, several seconds, minute, several minutes, hourly, several hours, daily, several days, weekly, monthly, etc.

Typically, the electrical energy output amplitude span of supported mobile communication or computing devices can range 10 times or more between extremes (i.e., +/−10× energy output); therefore, in one example, a glucose monitor connected to a mobile device may receive up to 100 times excess electrical energy (i.e., excessive electrical energy input) from the mobile device than required for charging. As used herein, the term "electrical energy" refers to energy which has been converted from electrical potential energy which, in turn, is being supplied by electric current and/or electrical potential that is delivered by an electrical circuit (e.g., $P=I \times V=I^2 \times R=V^2/R$). Typically, the electrical energy is measured in joules or electronvolts.

As used herein, "electrical power" is the rate at which electric energy is transferred by an electric circuit and is measured in watts (P), one joule per second. Electric power is transformed to other forms of energy when electric charges move through an electric potential (voltage) difference, which occurs in electrical components in electric circuits.

As used herein, the term "smart phone" or "mobile device" may relate to various communications and computing devices, for example, wearable computers, tablets, portable computers, smart watches etc.

In some embodiments, the system of the present invention is configured to: (i) measure an electrical power output of a mobile communications device, such as a smart phone, tablet, wearable device etc., where the electrical power output is directed to power a fluid testing apparatus (FTA), such as a glucose monitor (GM) dongle adapted to connect to a mobile device via an audio jack, hereinafter referred to within as an Adaptor; (ii) identify whether the electrical power output is substantially greater (i.e., 2×, 3×, 4×, 5×, 6×, 7×, 8×, 9×, 10×, etc.) than the electrical power required to power the FTA; (iii) if the electrical power output is substantially greater than the electrical power required to power the FTA, generate and send a first signal to the device to result in a first modification (i.e., reduction) of the electrical power output; (iv) measure a reduced electrical power output of the device; (v) identify whether the reduced electrical power output is substantially comparable (i.e., between 1×-1.99×) to the electrical power required to power the FTA; (vi) if the electrical power output is substantially greater than the electrical power required to power the FTA, generate and send a second signal to the device to result in a second modification (i.e., reduction) of the electrical power output of the reduced electrical power output measured (i.e., is not substantially comparable to the electrical power required to power the FTA); (vii) continue measuring, identifying, generating, etc. until the reduced electrical power output is substantially comparable; or any combination thereof.

In some embodiments, an electrical power output can be modified/reduced in measured/calculated increments. In some embodiments, the measured/calculated increment can range from 1%-50%. In some embodiments, the measured/calculated increment can range from 1%-40%. In some embodiments, the measured/calculated increment can range from 1%-30%. In some embodiments, the measured/calculated increment can range from 1%-20%. In some embodiments, the measured/calculated increment can range from 1%-10%. In some embodiments, the measured/calculated increment can range from 1%-5%. In some embodiments, the measured/calculated increment can range from 5%-50%. In some embodiments, the measured/calculated increment can range from 10%-50%. In some embodiments, the measured/calculated increment can range from 20%-50%. In some embodiments, the measured/calculated increment can range from 30%-50%. In some embodiments, the measured/calculated increment can range from 40%-50%.

In some embodiments, the present invention relates to system(s) and/or method(s) configured to adjust (e.g., self-adjust) a level of electrical power during a charging event of a testing apparatus or device (i.e., an audio-powered glucose monitoring device). In some embodiments, the system is configured to adjust the level of electrical power substantially in real time. In some embodiments, the system is configured to dynamically adjust the level of electrical power.

In some embodiments, the system of the present invention is configured to reduce printed circuit board ("PCB") heating of an audio-powered fluid resting apparatus, such as a glucose monitoring device, resulting from excessive electrical power input (e.g., but not limited to, 2×, 3×, 4×, 5×, 6×, 7×, 8×, 9×, 10×, etc. input electrical power than required for charging). In some embodiments, the system of the present invention is configured to result in a reduction of excessive electrical power on the PCB (i.e., heating of the entire circuit). In some embodiments, an ambient temperature can be used as a calculation parameter per Joule-Lenz law, e.g., per using the following equation to define the temperature coefficient:

$$R=R_0[1+\alpha(T-T_0)]$$

In some embodiments, the system of the present invention is configured to allow an increased battery life of the device (i.e., Smartphone device).

In some embodiments, the system of the present invention is configured to include an algorithm configured to reduce an output volume of electrical power provided by powerful devices (e.g., but not limited to Samsung smartphones, Apple smartphones, LG smartphones, etc.) until the minimum required level is reached.

In some embodiments, the system of the present invention is configured to include, but is not limited to: (i) a physical element (e.g., but not limited to, the FSK of audio over 3.5" jack connector); (ii) a virtual element (e.g., but not limited to, a link, which can represent a universal asynchronous receiver/transmitter (UART) data transfer protocol); (iii) a protocol (e.g., but not limited to, a protocol representing the command flow between the system of the mobile device and the FTA), or any combination thereof. In some embodiments of the system of the present invention, the algorithm (i.e., self-adjustment algorithm) is configured to be used in connection with the protocol of the system. In some embodiments, a hardware design of the FTA is configured to support a dynamic range of electrical power for starting up the microprocessor (mP) and/or supply communication processing. In some embodiments, the dynamic range of electrical power for starting up the microprocessor and/or supply communication processing is between 1 mW to 200 mW. In some embodiments, the dynamic range of electrical power for starting up the microprocessor and/or supply communication processing is between 50 mW to 200 mW. In some embodiments, the dynamic range of electrical power for starting up the microprocessor and/or supply communication processing is between 100 mW to 200 mW. In some embodiments, the dynamic range of electrical power for starting up the microprocessor and/or supply communication processing is between 150 mW to 200 mW. In some embodiments, the dynamic range of electrical power for starting up the microprocessor and/or supply communication processing is between 1 mW to 150 mW. In some embodiments, the dynamic range of electrical power for starting up the microprocessor and/or supply communication processing is between 1 mW to 100 mW. In some embodiments, the dynamic range of electrical power for starting up the microprocessor and/or supply communication processing is between 1 mW to 50 mW.

In some embodiments, the system of the present invention is configured to include a file with instructions, software or executable code, to execute commands to enable execution of instructions to maximize efficiency of an output of electrical power (i.e., voltage) for powering the FTA connected to a mobile device, by adjusting the FTA Power Adjust function. In some embodiments, the system (e.g., including FTA firmware (including, but not limited to, persistent memory, program code, data, etc.)) includes software configured to measure a test voltage, where the test voltage represents the power level of the device after an initial connection. In some embodiments, when a measurement of electrical power (i.e., voltage) identifies that the electrical power directed to the FTA is greater than/exceeds a required level, the system is configured to allow the FTA to enter a Power Adjustment mode. In some embodiments, software code, power management code etc. on the mobile device operates in parallel to the FTA, to coordinate power adjusting between the two devices.

In some embodiments, when a measurement of electrical power identifies that the amount of electrical power directed to the FTA is substantially similar to the required electrical power, the system is configured to allow the FTA to enter a Power Maintenance mode. In some embodiments, the system includes a switch (e.g. hardware and/or software driven switch, for example, as may be operated at step 5 in FIG. 5A), which allows the FTA to enter Power Maintenance mode. In some embodiments, when a switch is triggered, an alert is sent to the connected mobile device. In some embodiments, when the system enters/maintains the Power Maintenance mode, the system is configured to measure electrical power input less frequently. In some embodiments, the system does not include a power maintenance mode, where the system is configured to use a minimum power and the power adjustment. In some embodiments, the minimum power and the power adjustment is used during startup.

In some embodiments, the system of the present invention includes a switch (e.g. operated at step 5 in FIG. 5A), where the switch is configured to end a first mode, e.g., the Power Maintenance mode/Power Adjustment mode and enter a second mode, e.g., the Power Adjustment mode/Power Maintenance mode. In an exemplary embodiment, the switch is turned on when a power measurement is taken, when measured while in the Power Maintenance mode, is greater than an allowable pre-set power input, triggering entry into the Power Adjustment mode. In an exemplary embodiment, the switch is turned on when a power measurement is taken, when measured while in the Power Adjustment mode, is substantially similar to an allowable pre-set power input, triggering entry into the Power Maintenance mode. In some embodiments, the system is configured to send an alert when the switch is triggered when in a first power mode (Power Adjustment mode/Power Maintenance mode) and initiates the entry into the second power mode (Power Maintenance mode/Power Adjustment mode).

In some embodiments, the system of the present invention includes a Power Adjustment mode, where the system is configured to allow a FTA to transmit/send a command to the software of the system, where the command allows for a reduction of the output volume by an increment (e.g., but not limited to, 5%, 10%, 15%, 20%, 25%, 30%, 35%, 40%, 45%, 50%, etc.) of the power input. In some embodiments of the system of the present invention, the system is configured to (1) adjust the power (i.e., volume); (2) send an acknowledgement command to the FTA; (3) allow the FTA FW to check the test voltage, or any combination thereof. In some embodiments, an adjustment of power/volume by the software of the system results in generating a command (e.g., an acknowledgement command) and sends the command to the FTA, allowing the FTA FW to measure the test voltage. In some embodiments, the adjustment of power/volume by the software of the system repeats until the FTA measurement indicates that the test voltage falls within the allowed range.

In some embodiments, the system of the present invention is configured to send a command (e.g., a "PowerOK" affirmative command) to the FTA and/or mobile device when the Power Adjustment mode is completed (i.e., upon entry into Power Maintenance mode). In some embodiments, the command is received by the system and allows for the entry into a power-saving mode (i.e., Power Maintenance mode) allowing the device to (1) save the measurement of the resulting voltage/energy level and (2) identify the resulting voltage/energy level associated with the FTA (i.e., "optimal voltage level(s)" for the device), and (3) create a FTA identifier, where the FTA identifier contains the information associated with the voltage adjustment/optimal voltage level(s). In some embodiments, the next time the FTA is connected to the mobile device (i.e., through a connection initialization phase at the audio port), the system is configured to identify the FTA by the FTA identifier and reduce the power to the previously stored/saved value (i.e., optimal voltage level) associated with the FTA (e.g., instantly, in real-time). In some embodiments, the FTA identifier allows for a reduction in startup time of the system by reducing and/or removing the Power Adjustment phase.

In some embodiments, the system of the present invention is configured to receive an input, where the input is the switching a microphone off from the power circuit (e.g., but not limited to, when the power is measured at a greater level required).

FIG. 1 is a schematic diagram of an example of a network environment in which the present invention may operate, according to some embodiments. As can be seen, FIG. 1 illustrates one embodiment of an environment, in which system 100 for adjusting power levels on a monitoring device may operate. However, not all of these components may be required to practice the invention, and variations in the arrangement and type of the components may be made without departing from the spirit or scope of the invention.

In some embodiments, the inventive system and method may include a large number of members and/or concurrent transactions. In other embodiments, the inventive system and method are based on a scalable computer and network architecture that incorporates varies strategies for assessing the data, caching, searching, and database connection pooling. An example of the scalable architecture is an architecture that is capable of operating multiple servers.

In some embodiments, members of the system 100 may include virtually any computing device 102-104 capable of receiving and sending a message over a network, such as network 105, to and from another computing device, such as servers 106 and 107, each other, and the like. Of course, many servers may be used, specifically or in combination, to serve devices, users, and managers of the system. In embodiments, the set of such devices includes devices that typically connect using a wired communications medium such as personal computers, multiprocessor systems, microprocessor-based or programmable consumer electronics, network PCs, and the like. In embodiments, the set of such devices also includes devices that typically connect using a wireless communications medium such as cell phones, smart phones, pagers, walkie-talkies, radio frequency (RF) devices, infrared (IR) devices, CBs, integrated devices combining one or more of the preceding devices, or virtually any mobile device, and the like. Similarly, in embodiments, client devices 102-104 are any device that is capable of connecting to a communications network using a wired or wireless communication medium, such as a smart phone, tablet, PDA, POCKET PC, wearable computer, and any other device that is equipped to communicate over a wired and/or wireless communication medium.

In embodiments, each member device within member devices 102-104 may include a browser application that is configured to receive and to send web pages, and the like. In embodiments, the browser application may be configured to receive and display graphics, text, multimedia, and the like, employing virtually any web based language, including, but not limited to Standard Generalized Markup Language (SMGL), such as HyperText Markup Language (HTML), a wireless application protocol (WAP), a Handheld Device Markup Language (HDML), such as Wireless Markup Language (WML), WMLScript, XML, JavaScript, and the like. In embodiments, programming may include either Java, .Net, QT, C, C++ or other suitable programming language.

In embodiments, member devices 102-104 may be further configured to receive a message from another computing device employing another mechanism, including, but not limited to email, Short Message Service (SMS), Multimedia Message Service (MMS), instant messaging (IM), internet relay chat (IRC), mIRC, Jabber, and the like or a Proprietary protocol.

In some embodiments, network 105 may be configured to couple one computing device to another computing device to enable them to communicate. In some embodiments, network 105 may be enabled to employ any form of computer readable media for communicating information from one electronic device to another. Also, in embodiments, network 105 may include a wireless interface, and/or a wired interface, such as the Internet, in addition to local area networks (LANs), wide area networks (WANs), direct connections, such as through a universal serial bus (USB) port, other forms of computer-readable media, or any combination thereof. In embodiments, on an interconnected set of LANs, including those based on differing architectures and protocols, a router may act as a link between LANs, enabling messages to be sent from one to another.

Also, in some embodiments, communication links within LANs typically include twisted wire pair or coaxial cable, while communication links between networks may utilize analog telephone lines, full or fractional dedicated digital lines including T1, T2, T3, and T4, Integrated Services Digital Networks (ISDNs), Digital Subscriber Lines (DSLs), wireless links including satellite links, or other communications links known to those skilled in the art. Furthermore, in some embodiments, remote computers and other related electronic devices could be remotely connected to either LANs or WANs via a modem and temporary telephone link. In essence, in some embodiments, network 105 includes any communication method by which information may travel between client devices 102-104, and servers 106 and 107.

Figure 2:
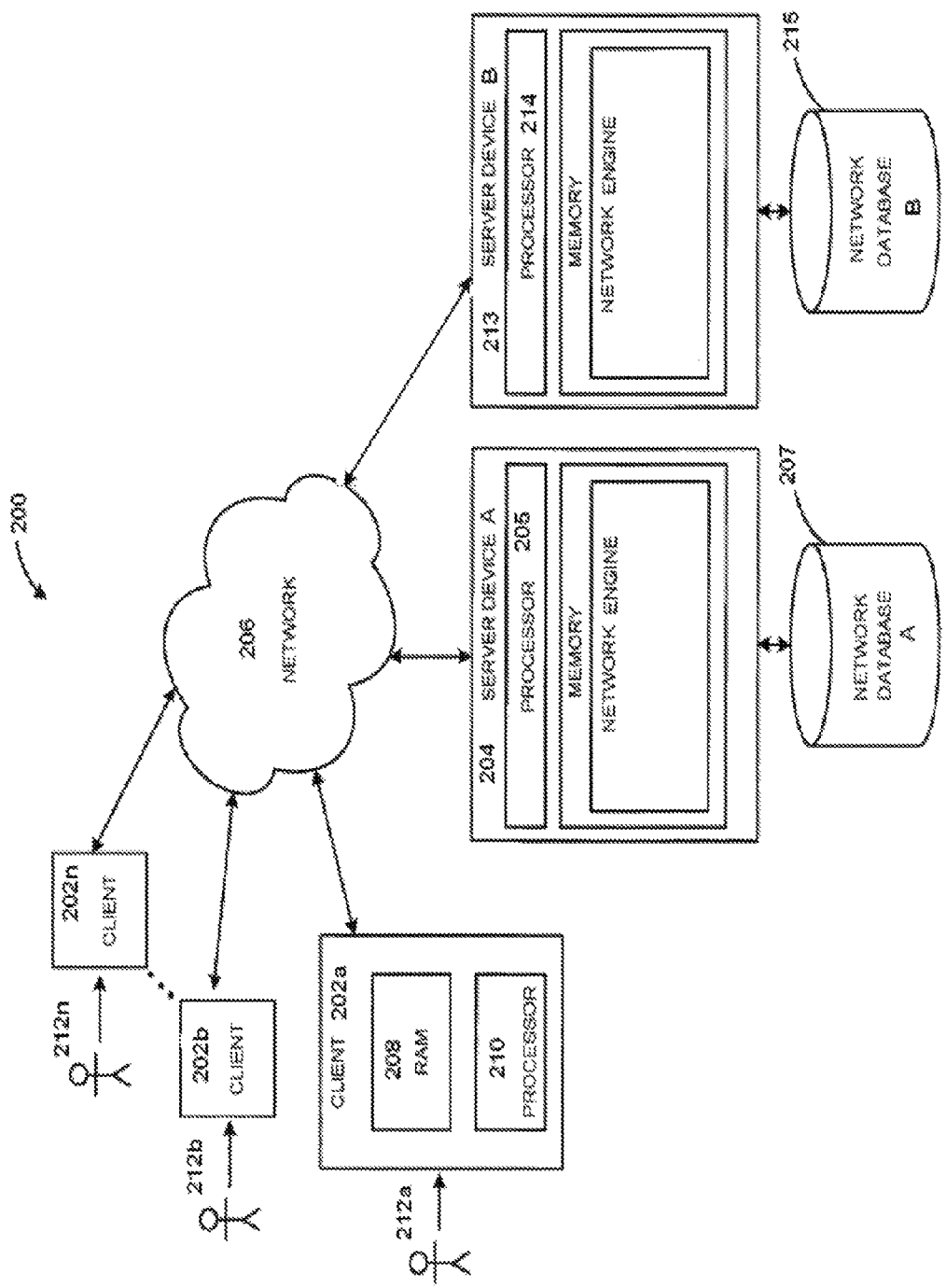
FIG. 2 is a schematic diagram of second example of an exemplary embodiment of the computer and network architecture that supports the methods and systems, according to some embodiments.

FIG. 2 is a schematic diagram of second example of an exemplary embodiment of the computer and network architecture that supports the methods and systems, according to some embodiments. As can be seen, FIG. 2 shows system 200 for adjusting power levels on a monitoring device. In some embodiments, the member devices 202a, 202b through 202n shown each at least includes a computer-readable medium, such as a random access memory (RAM) 208 coupled to a processor 210 or FLASH memory. In some embodiments, the processor 210 may execute computer-executable program instructions stored in memory 208. In some embodiments, such processors comprise a microprocessor, an ASIC, and state machines. In some embodiments, such processors comprise, or may be in communication with, media, for example computer-readable media, which stores instructions that, when executed by the processor, cause the processor to perform the steps described herein. Embodiments of computer-readable media may include, but are not limited to, an electronic, optical, magnetic, or other storage or transmission device capable of providing a processor, such as the processor 210 of client 202a, with computer-readable instructions. In some embodiments, other examples of suitable media may include, but are not limited to, a floppy disk, CD-ROM, DVD, magnetic disk, memory chip, ROM, RAM, an ASIC, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. In some embodiments, the instructions may comprise code from any computer-programming language, including, for example, C, C++, Visual Basic, Java, Python, Perl, and JavaScript.

In some embodiments, member devices 202a-n may also comprise a number of external or internal devices such as a mouse, a CD-ROM, DVD, a keyboard, a display, or other input or output devices. Examples of client devices 202a-n may be personal computers, digital assistants, personal digital assistants, cellular phones, mobile phones, smart phones, pagers, digital tablets, laptop computers, Internet appliances, and other processor-based devices. In general, a client device 202a may be any type of processor-based platform that is connected to a network 206 and that interacts with one or more application programs. Client devices 202a-n may operate on any operating system capable of supporting a browser or browser-enabled application, such as Microsoft™, Windows™, or Linux. The client devices 202a-n shown may include, for example, personal computers executing a browser application program such as Microsoft Corporation's Internet Explorer™, Apple Computer, Inc.'s Safari™, Mozilla Firefox, and Opera. Through the client devices 202a-n, users, 212a-n communicate over the network 206 with each other and with other systems and devices coupled to the network 206. As shown in FIG. 2, server devices 204 and 213 may be also coupled to the network 206. In an embodiment of the present invention, one or more clients can be a mobile client.

In some embodiments, the term "mobile electronic device" may refer to any portable electronic device that may or may not be enabled with location tracking functionality. For example, a mobile electronic device can include, but is not limited to, a mobile phone, Personal Digital Assistant (PDA), Blackberry™ Pager, Smartphone, tablet or any other reasonable mobile electronic device. For ease, at times the above variations are not listed or are only partially listed, this is in no way meant to be a limitation.

In some embodiments, the terms "proximity detection," "locating," "location data," "location information," and "location tracking" as used herein may refer to any form of location tracking technology or locating method that can be used to provide a location of a mobile electronic device, such as, but not limited to, at least one of location information manually input by a user, such as, but not limited to entering the city, town, municipality, zip code, area code, cross streets, or by any other reasonable entry to determine a geographical area; Global Positions Systems (GPS); GPS accessed using Bluetooth™; GPS accessed using any reasonable form of wireless and/or non-wireless communication; WiFi™ server location data; Bluetooth™ based location data; triangulation such as, but not limited to, network based triangulation, WiFi™ server information based triangulation, Bluetooth™ server information based triangulation; Cell Identification based triangulation, Enhanced Cell Identification based triangulation, Uplink-Time difference of arrival (U-TDOA) based triangulation, Time of arrival (TOA) based triangulation, Angle of arrival (AOA) based triangulation; techniques and systems using a geographic coordinate system such as, but not limited to, longitudinal and latitudinal based, geodesic height based, Cartesian coordinates based; Radio Frequency Identification such as, but not limited to, Long range RFID, Short range RFID; using any form of RFID tag such as, but not limited to active RFID tags, passive RFID tags, battery assisted passive RFID tags; or any other reasonable way to determine location. For ease, at times the above variations are not listed or are only partially listed, this is in no way meant to be a limitation.

In some embodiments, near-field wireless communication (NFC) can represent a short-range wireless communications technology in which NFC-enabled devices are "swiped," "bumped," "tap" or otherwise moved in close proximity to communicate. In some embodiments, NFC could include a set of short-range wireless technologies, typically requiring a distance of 10 cm or less.

In some embodiments, NFC may operate at 13.56 MHz on ISO/IEC 18000-3 air interface and at rates ranging from 106 kbit/s to 424 kbit/s. In some embodiments, NFC can involve an initiator and a target; the initiator actively generates an RF field that can power a passive target. In some embodiment, this can enable NFC targets to take very simple form factors such as tags, stickers, key fobs, or cards that do not require batteries. In some embodiments, NFC peer-to-peer communication can be conducted when a plurality of NFC-enable devices within close proximity of each other.

In some embodiments, use of NFC peer-to-peer communication can provide estimates of the optimal energy ranges for the system of the present invention, thus reducing the number of times the Power Adjustment mode is required to achieve optimal voltage level(s).

For purposes of the instant description, the terms "cloud," "Internet cloud," "cloud computing," "cloud architecture," and similar terms correspond to at least one of the following: (1) a large number of computers connected through a substantially real time communication network (e.g., Internet); (2) providing the ability to run a program or application on many connected computers (e.g., physical machines, virtual machines (VMs)) at the same time; (3) network-based services, which appear to be provided by real server hardware, and are in fact served up by virtual hardware (e.g., virtual servers), simulated by software running on one or more real machines (e.g., allowing to be moved around and scaled up (or down) on the fly without affecting the end user). In some embodiments, the inventive FTA power adjustment/maintenance system offers/manages the cloud computing/architecture as, but not limiting to: infrastructure a service (IaaS), platform as a service (PaaS), and software as a service (SaaS).

Figure 3:
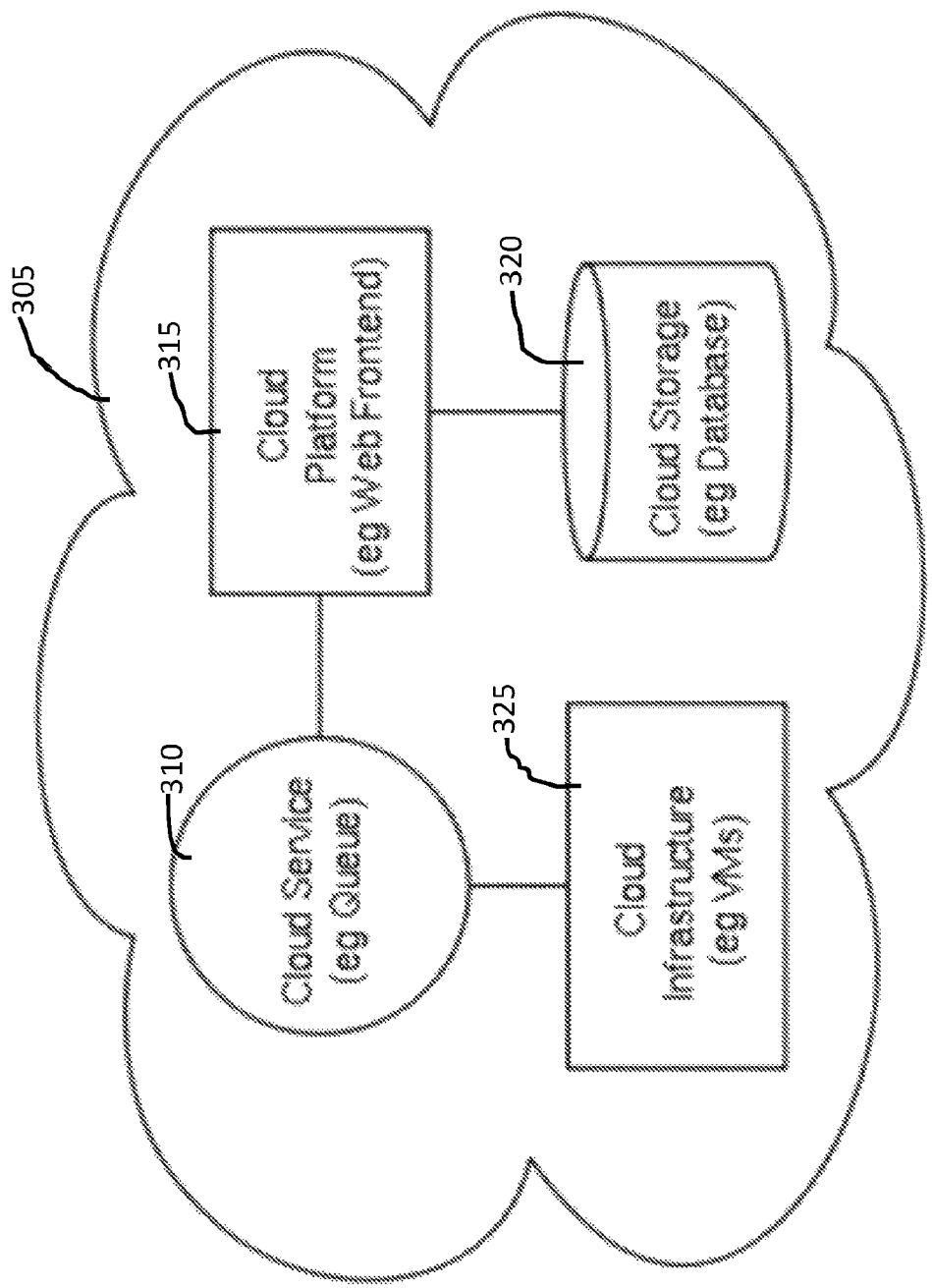
FIG. 3 is a schematic diagram of an exemplary implementation of a cloud computing/architecture that supports the methods and systems, according to some embodiments.

FIG. 3 is a schematic diagram of an exemplary implementation of a cloud computing/architecture that supports the methods and systems, according to some embodiments. As can be seen, communications network 305 includes a cloud service module 310, Cloud Infrastructure 325, a Cloud platform 315, and Cloud storage element 320. In some embodiments, the power level adjustment means in the FTA and/or the mobile device is connected to a memory having stored therein power level adjustment data.

Figure 4:
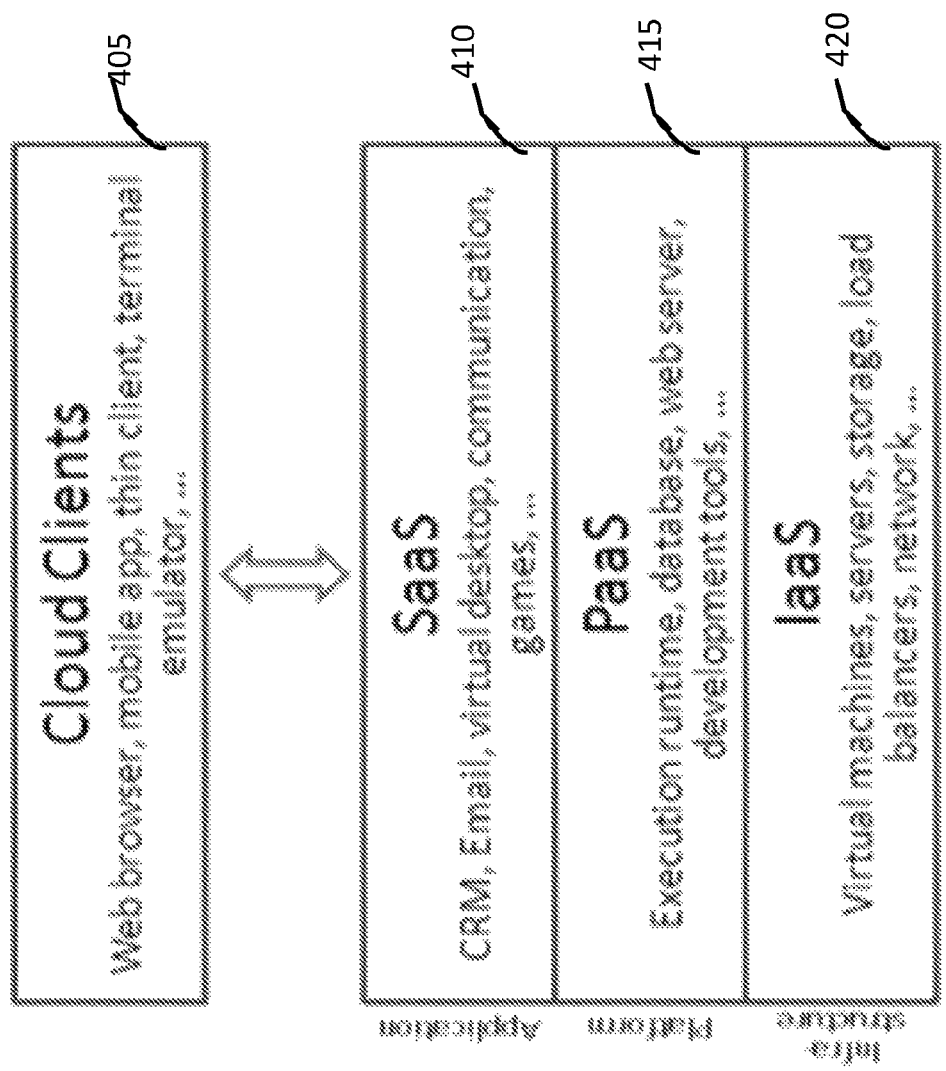
FIG. 4 is a schematic flow diagram showing the connections between components in an exemplary implementation of a cloud system that supports the methods and systems, according to some embodiments.

FIG. 4 is a schematic flow diagram showing the connections between components in an exemplary implementation of a cloud system that supports the methods and systems, according to some embodiments. As can be seen, end users using devices or computers connected to the communications cloud 405, for example, using a Web browser, mobile Application, thin client, terminal emulator etc., can connect to various Applications 410, Platforms 415, and/or Infrastructures 420.

It is noted that the embodiments described herein may, of course, be implemented using any appropriate computer system hardware and/or computer system software. In this regard, those of ordinary skill in the art are well versed in the type of computer hardware that may be used (e.g., a mainframe, a mini-computer, a personal computer ("PC"), a network (e.g., an intranet and/or the internet)), the type of computer programming techniques that may be used (e.g., object oriented programming), and the type of computer programming languages that may be used (e.g., C++, Basic, AJAX, Javascript). The aforementioned examples are, of course, illustrative and not restrictive.

Figure 5A:
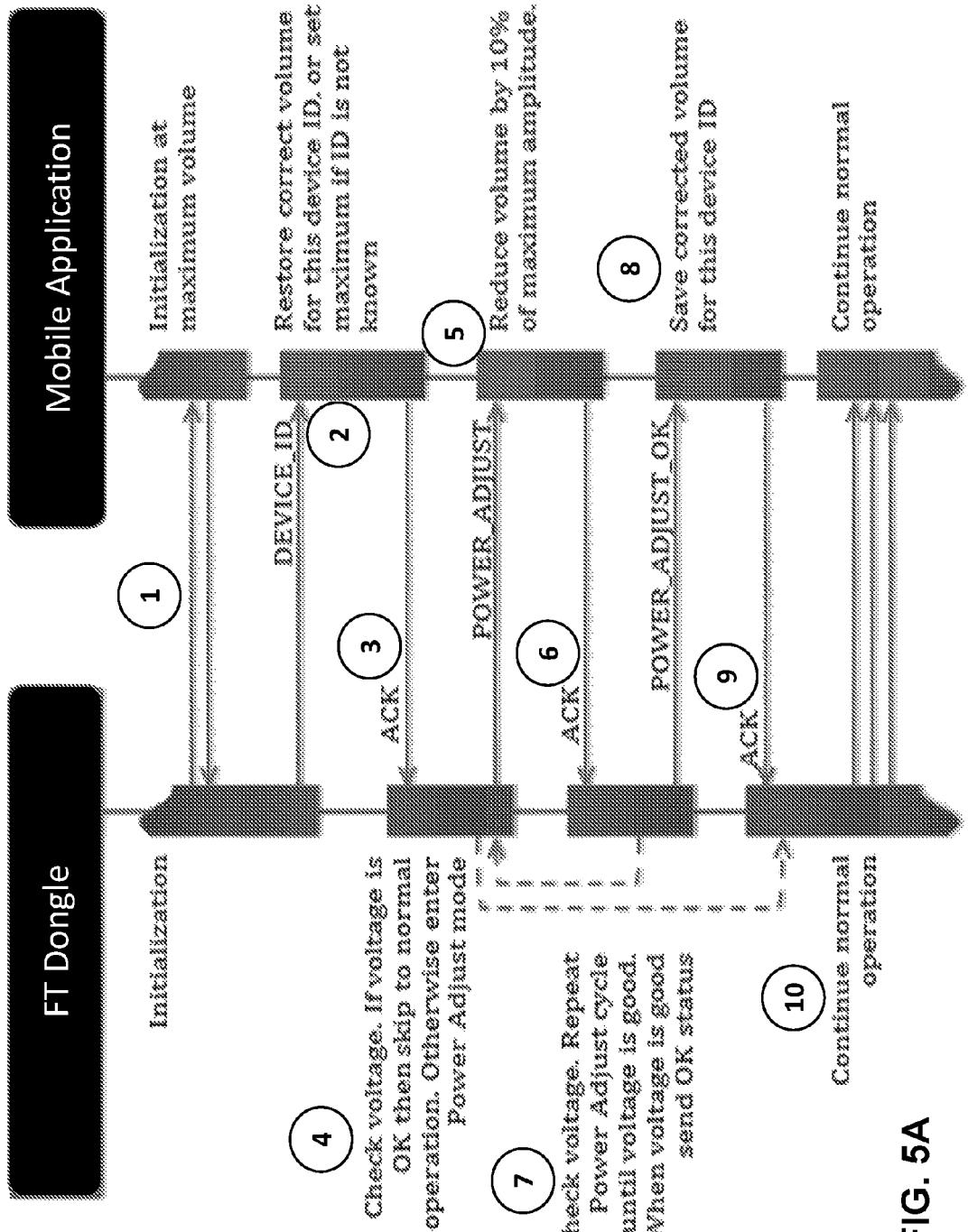
FIGS. 5A and 5B are a work flow diagrams illustrating the steps or operations, according to some embodiment of the present invention, showing the steps involved in adjusting power being sent to the external connector device or dongle.
Figure 5B:
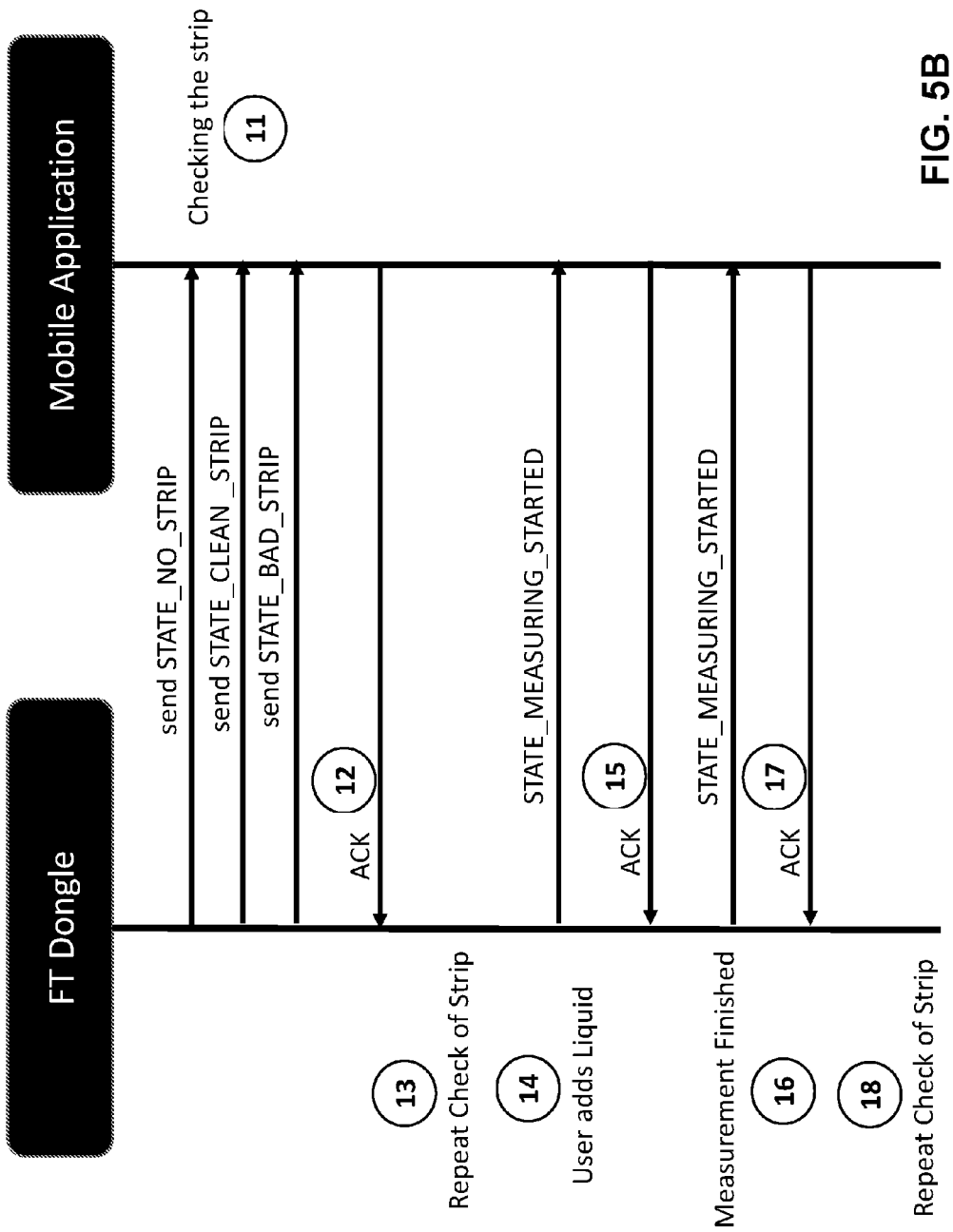

FIGS. 5A and 5B illustrate an embodiment of the present invention, showing the steps involved in adjusting power being sent to the FTA. In some embodiments, acknowledging messages "ACK" are sent by the system once a step is completed (e.g., reduction in voltage).

In accordance with some embodiments, one or more of the following steps may be executed to adjust the power being sent to the FTA. It is noted that the order of steps described below may be reversed or otherwise ordered, as may be necessary. At step 1: FTA Dongle Initialization is executed, whereby the FTA sends a DEVICE_CONNECT_REQUEST to the mobile device. Upon receipt of the request, the initialized mobile application sets the mobile device volume to a maximum state.

At step 2, the FTA Dongle sends a DEVICE_ID to the mobile device. If the Device ID is known, the correct volume of mobile device may be restored for this DEVICE_ID (i.e. at an effective level to enable operation of the FTA Dongle. In such a case, the optimum working power level for a device will generally be stored on the mobile device, for example, in the user default settings for the mobile application. If the Device_ID is not known, the mobile device may be maintained, optionally temporarily, at maximum volume for this Device.

At step 3, the Mobile device returns an acknowledging message to the FTA.

At step 4, the FTA checks the voltage. For example: Option 1—If the voltage is fine, the self-test is passed, and the FTA is ready to take measurements. Option 2—If the voltage is high, the FTA will initialize Power Adjust mode.

At step 5, the FTA launches POWER_ADJUST mode, optionally using a switch, which includes sending a POWER_ADJUST message to the Mobile device. The mobile device subsequently reduces volume by, for example, 10% of the maximum amplitude. Of course, other increments or combinations of increments may be used.

At step 6, the Mobile device returns an acknowledging message to the FTA.

At step 7, the FTA checks the voltage. For example— Option 1: If the voltage is high, the FTA may initialize Power Adjust mode, and repeat steps 5-7, until the voltage is good or effective. Option 2—If the voltage is effective, the FTA may generate a POWER_ADJUST_OK message.

At step 8, the FTA sends the POWER_ADJUST_OK message, causing the mobile device to save the corrected volume for this FTA device ID.

At step 9, the Mobile device returns acknowledging message to the FTA

At step 10, the self-test is considered as having been passed, whereinafter, the FTA is ready to continue with normal operation, for example, to record and process fluid or other measurements.

At step 11, in order to check a strip by the FTA, the following examples of options may be executed: Option 1—FTA sends a STATE_NO_STRIP message in case no strip inside the FTA Dongle.

Option 2—FTA sends a STATE_CLEAN_STRIP message in case a clean strip inserted. Option 3—FTA sends a STATE_BAD_STRIP message in case a used strip inserted.

At step 12, the Mobile device returns an acknowledge message to the FTA.

At step 13, the FTA repeats the check strip step, in case the strip is changed.

At step 14, a user adds liquid for testing, for example, a drop of blood. FTA sends a STATE_MEASURING_STARTED message.

At step 15, the Mobile device returns acknowledging message to the FTA.

At step 16, when the measurement is finished, the FTA sends a DEVICE_GDATA message with the measurement result.

At step 17, the Mobile device returns an acknowledge message to the FTA.

At step 18, FTA Repeats the FTA check strip step, in case the strip is changed.

Of course, other steps or combinations of steps may be used.

In still further embodiments, a step of automatic volume reduction to a selected or default level may be initiated, following completion of a measurement process and/or closing of the mobile device medical device measurement application. In one example, the device sound is returned to the level it was previously at before the mobile device medical device measurement application changed the volume. For example, the mobile device may take a sound snapshot at the start of the measurement process, in order to know what level to return the sound to after the measurement procedure. In another example, the mobile device may return the sound level of the mobile device to a default level, such as an average volume, after the measurement procedure. In a still further example, the user may determine in the settings of the mobile device medical device measurement application to return the volume of the mobile device to a selected level, after the measurement procedure.

While a number of embodiments of the present invention have been described, it is understood that these embodiments are illustrative only, and not restrictive, and that many modifications may become apparent to those of ordinary skill in the art. Further still, the various steps may be carried out in any desired order (and any desired steps may be added and/or any desired steps may be eliminated).

What is claimed is:

1. A health management system for performing a parameter measurement in a fluid sample, comprising:
   a. a mobile communications device with an application to perform health management for one or more health related conditions;
   b. a strip adapted to absorb a fluid sample and to produce a signal indicative of the parameter level in the sample; and
   c. a fluid testing apparatus for obtaining an analog measurement of the fluid parameter, the fluid testing apparatus including an adaptor to connect the strip to the mobile communications device to thereby allow delivery of the produced signal or a correlated signal to the mobile communications device for obtaining a measurement of the fluid parameter displayed on the mobile communications device, wherein the fluid testing apparatus relies on the mobile communications device for at least one of power supply and display means;
   and wherein the system includes a power level adjustment means associated with the device audio jack, the adaptor, or a combination thereof, for providing an electrical power output to operate the fluid testing apparatus when the power level adjustment means is connected to the mobile communications device,
   wherein the power level adjustment means is configured to dynamically modify in real time the electrical power output from the mobile communications device.

2. The system of claim 1, wherein the power level adjustment means are adapted to modify the electrical power output from the communications device in calculated increments.

3. The system of claim 1, wherein the power level adjustment means are configured to reduce printed circuit board heating of an audio-powered fluid resting apparatus, resulting from excessive electrical power input.

4. The system of claim 1, wherein the power level adjustment means are configured to increase battery life of the mobile communications device.

5. The system of claim 1, wherein the power level adjustment means are configured to reduce an output volume of electrical power provided by the mobile communications device.

6. The power level adjustment means of claim 1, wherein the power level adjustment means include a file with instructions to execute commands to enable execution of instructions to maximize efficiency of an output of electrical power for powering the FTA connected to the mobile device.

7. The power level adjustment means of claim 1, wherein the power level adjustment means is connected to a memory in the mobile communications device having stored therein power level adjustment data.

8. A blood testing apparatus for performing glucose measurement in a blood sample comprising:
   a. a glucose strip adapted to absorb a blood sample and to produce a signal indicative of the glucose level in the blood sample; and
   b. an adaptor adapted to connect the glucose strip to a mobile communications device to thereby allow delivery of the produced signal or a correlated signal to the mobile communications device for obtaining a measurement of the glucose level displayed on the mobile communications device, wherein the blood testing apparatus relies on the mobile communications device at least for a power supply and display means, and wherein the mobile communications device includes a power level adjustment means associated with the device audio jack, for providing an electrical power output to operate the blood testing apparatus,
   wherein the power level adjustment means is configured to dynamically modify in real time the electrical power output from the mobile communications device.

9. A method for performing a fluid parameter measurement in a fluid sample comprising the steps of:
   a. installing a dedicated application software on a mobile communications device;
   b. loading a fluid sample on a fluid testing apparatus, the apparatus comprising: a strip to absorb such sample and to produce a signal indicative of the parameter level in the sample; and an adaptor adapted to connect the strip to a smart phone to thereby allow delivery of the produced signal or a correlated signal to the mobile communications device for obtaining a measurement of the fluid parameter displayed on the mobile communications device, wherein the testing apparatus relies on the mobile communications device at least for a power supply and display means;
   c. inserting the loaded fluid testing apparatus into a headset jack of a mobile communications device to thereby allow communication between the apparatus and the mobile communications device and delivery of power supply; and
   d. obtaining the measured parameter level displayed on the smart mobile communications device;
   wherein the mobile communications device includes a power level adjustment means associated with the communications device audio jack, for providing an electrical power output to operate the fluid testing apparatus,
   wherein the power level adjustment means is configured to dynamically modify in real time the electrical power output from the mobile communications device.

10. The method of claim 9, wherein the volume of the mobile communications device is automatically reduced to a selected level following an end of a fluid measurement process.

11. A mobile hand held laboratory system capable of performing fluid parameter measurement of a sample, the system comprising:
   a. a mobile communications device installed with a dedicated application software;
   b. a strip adapted to absorb a fluid sample and to produce a signal indicative of the parameter level in the sample; and
   c. an adaptor adapted to connect said strip to a mobile communications device to thereby allow delivery of the produced signal or a correlated signal to the mobile communications device for obtaining a measurement of the fluid parameter displayed on the mobile communications device, wherein the testing apparatus relies on the mobile communications device for at least for a power supply and display means, and wherein the mobile communications device, the adaptor, or any combination thereof, includes a power level adjustment means associated with the device audio jack, for providing an electrical power output to operate the fluid testing apparatus,
   wherein the power level adjustment means is configured to dynamically modify in real time the electrical power output from the mobile communications device.

* * * * *